United States Patent [19]

Andreasson et al.

[11] Patent Number: 4,990,269

[45] Date of Patent: Feb. 5, 1991

[54] SURFACE ACTIVE COMPOUND, A MICROEMULSION CONTAINING SAID COMPOUND AND THE USE THEREOF

[75] Inventors: Eva M. Andreasson, Gothenburg; Krister A. Holmberg, Molndal; Borje Nystrom, Knivsta; Eva M. Osterberg, Gothenburg, all of Sweden; Finn Egeli, Stavanger, Norway

[73] Assignees: Berol Kemi AB, Stenungsund, Sweden; Tendex Kjemi Service A/S, Stavanger, Norway

[21] Appl. No.: 411,195

[22] Filed: Sep. 21, 1989

Related U.S. Application Data

[63] Continuation-in-part of Ser. No. 117,538, Nov. 6, 1987, abandoned, which is a continuation-in-part of Ser. No. 814,060, Dec. 27, 1985, abandoned.

[30] Foreign Application Priority Data

Jan. 3, 1985 [NO] Norway ................................. 850027

[51] Int. Cl.$^5$ ............................................. E21B 43/22
[52] U.S. Cl. ................................................... 252/8.554
[58] Field of Search ............ 252/8.554, 312, DIG. 14, 252/551

[56] References Cited

U.S. PATENT DOCUMENTS

| 3,508,611 | 4/1970 | Davis et al. | 252/8.554 X |
| 3,981,361 | 9/1976 | Healy | 252/8.554 X |
| 4,018,278 | 4/1977 | Shupe | 252/8.554 X |
| 4,293,428 | 10/1981 | Gale et al. | 252/8.554 |
| 4,469,621 | 9/1984 | Kunitake et al. | 252/353 |
| 4,515,701 | 5/1985 | Hoskin | 252/8.554 |
| 4,592,875 | 6/1986 | Kesling et al. | 252/551 |
| 4,882,075 | 11/1989 | Jones | 252/8.554 X |
| 4,886,120 | 12/1989 | Shupe | 252/8.554 X |
| 4,894,173 | 1/1990 | Loza et al. | 252/8.554 |
| 4,931,218 | 6/1990 | Schenker et al. | 252/551 |
| 4,944,346 | 7/1990 | Grey et al. | 252/8.554 |

FOREIGN PATENT DOCUMENTS

| 1388251 | 3/1975 | United Kingdom . |
| 1479155 | 7/1977 | United Kingdom . |
| 1559823 | 1/1980 | United Kingdom ................ 252/551 |
| 1579167 | 11/1980 | United Kingdom . |

*Primary Examiner*—Robert L. Stoll
*Assistant Examiner*—Gary L. Geist
*Attorney, Agent, or Firm*—Watson, Cole, Grindle & Watson

[57] ABSTRACT

A surface active compound for use in microemulsions useful in oil recovery, wood impregnating, dry cleaning, cleaning of hard surfaces and for floor polishing, which has one hydrophobic group, containing 9–50, preferably 12–35 carbon atoms and 2–6 separate hydrophilic end groups, at least one of the hydrophilic end groups being a nonionic group obtained by reacting a compound having a reactive hydrogen atom with an alkylene oxide having 2–4 carbon atoms and at least one being an anionic group.

8 Claims, No Drawings

SURFACE ACTIVE COMPOUND, A MICROEMULSION CONTAINING SAID COMPOUND AND THE USE THEREOF

CROSS-REFERENCE TO RELATED APPLICATION

The present application is a continuation-in-part application of Ser. No. 117,538, filed Nov. 6, 1987, now abandoned which is a continuation-in-part of Ser. No. 814,060, filed Dec. 27, 1985, now abandoned.

BACKGROUND OF INVENTION

The present invention relates to a surface active compound which, due to its structure, has an excellent ability to form microemulsions. The surface active compound and the microemulsion containing the surface active compound could be used, e.g., in enhanced oil recovery, wood impregnation, dry cleaning, cleaning of hard surfaces and floor polishing.

THE PRIOR ART

Microemulsions have been known for a long time. The term was coined by Schulman in 1943 and since that time a substantial amount of literature dealing with various aspects of microemulsions has appeared. (For a review, see L. M. Prince, Microemulsions, Academic Press, N.Y. 1977).

Microemulsions are made from water, an oil component and a surfactant system. The surfactant system traditionally consists of a true surfactant (in the following referred to as "surfactant") and a cosurfactant. The surfactant may be anionic, nonionic, cationic or amphoteric. The cosurfactant (which is sometimes referred to as cosolvent or solubilizing agent) is normally an alkanol having from 3 to 6 carbon atoms, but other types of compounds, such as glycol ethers and amines, may also be used. The cosurfactant is usually a considerably smaller molecule than the surfactant and its role is to affect the molecular packing at the droplet interface in such a way that formation of a microemulsion is energetically favoured.

One of the most interesting application areas for microemulsions is surfactant flooding for enhanced oil recovery. Surfactant flooding means injection of a surfactant solution or a microemulsion into a reservoir with a view to decreasing the oil-water interfacial tension and, as a consequence, increase the amount of oil recovered by flooding.

In a high surfactant concentration systems a middle phase microemulsion in equilibrium with excess oil and brine forms if the surfactant system is well balanced. The existence of the middle phase microemulsion is considered a necessary condition in order to obtain a satisfactory oil recovery. The microemulsion phase gives an extremely low interfacial tension against brine, as well as oil. It has the ability to mobilize oil blocked in narrow pores, it causes coalescence of oil droplets and it ultimately brings about formation of a continuous oil bank which is pushed forward towards the production hole by a water slug.

The formation and preservation of a microemulsion is, consequently, of utmost importance for a successful result in chemical flooding. However, microemulsions are known to be sensitive to changes in composition. They normally only exist within fairly narrow intervals with regard to surfactant to cosurfactant ratio. During the flooding process a certain degree of separation between the surfactant and cosurfactant is likely to occur. This separation may be caused either by one of the components adsorbing more strongly to the surface of the formation than the other, or by unequivalent distribution of the two components between the oil and brine phases. A change in composition due to selective precipitation of degradation of one of the components is also conceivable. Consequently, even with well balanced systems showing only minor differences between the components with regard to adsorption and distribution between the phases, a gradual change of system composition will take place and the microemulsion will eventually break. Since the distances to be covered by a microemulsion in chemical flooding are often very long, the long-term preservation of the optimum system is regarded as a major issue for the use of the surfactant flooding technique for enhanced oil recovery.

The problem with selective separation of the surfactant and cosurfactant will also occur in other application areas for microemulsions. For example, when using microemulsions in wood impregnation, dry cleaning, cleaning of hard surfaces and floor polishing, the ratio between the surfactant and cosurfactant will gradually change.

SUMMARY OF INVENTION

It has now been found that both the surfactant and the cosurfactant functions can be built into one molecule. By using the surface active compounds of the invention, microemulsions can be prepared without the addition of further components. In this way the risk of a gradual separation of the surfactant and cosurfactant of the microemulsion is eliminated.

The surface active compound of the present invention has one hydrophobic group, containing 9–50, preferably 12–35, carbon atoms and 2–6 separate hydrophilic end groups, at least one of the latter being a non-iononic group obtained by reacting a compound having a reactive hydrogen atom with an alkylene oxide having 2–4 carbon atoms and at least one being an anionic group.

Compounds meeting this basic definition are those having the general formula

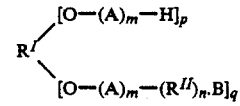

where $R^I$ is a hydrophobic group containing 9–50, preferably 12–35, carbon atoms and optionally functional groups such as ether and hydroxyl, $R^{II}$ is an alkylene or hydroxyalkylene group with 1–4 carbon atoms, A is an alkyleneoxy group derived from an alkylene oxide having 2–4 carbon atoms, m, which may be different for each branch (p and/or q), has an average value of 1–10, preferably 1–5, n is 0 or 1, p and q are 1–5, the sum p+q is 2–6, and B is an anionic group.

In the case n is 1, the anionic group is preferably carboxylate, phosphonate or sulphonate. When n is 0, the anionic group is preferably a sulphate, phosphate or phosphite. As mentioned, the group $R^I$ may contain functional groups. Examples of suitable functional groups are ether, ester, hydroxyl, amine thioether, sulfoxide, sulfone and carbamate. Of these functional groups, ether and hydroxyl are the preferred ones. In its end position, $R^I$ preferably contains a hydrocarbon group having 10-24 carbon atoms. The alkyleneoxy groups are preferably to at least 50% ethyleneoxy groups.

Specific examples of surface active agents according to the invention are

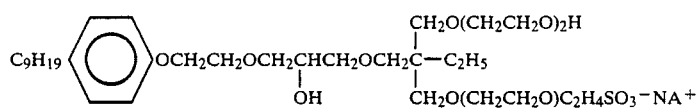
(a)

A = CH CH₂O, m = 2, p = 1, $R^{II}$ = C₂H₄, n = 1, B = SO₃⁻, q = 1, m = 1

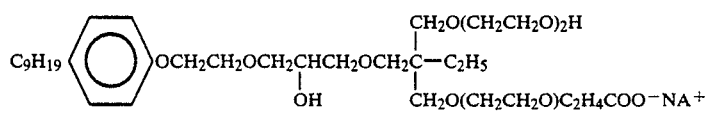
(b)

A = CH₂CH₂O, m = 2, p = 1, $R^{II}$ = C₂H₄, n = 1, B = COO⁻, q = 1, m = 1

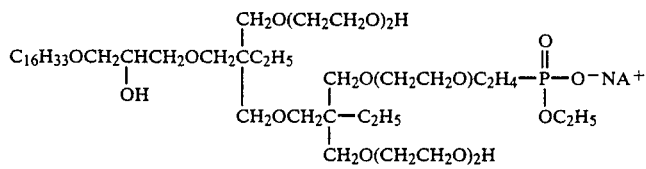
(c)

A = CH₂CH₂O, p = 2, m = 2 for each brance p, $R^{II}$ = C₂H₄, n = 1,

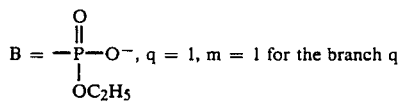

B = $-\overset{O}{\underset{OC_2H_5}{\overset{\|}{P}}}-O^-$, q = 1, m = 1 for the branch q

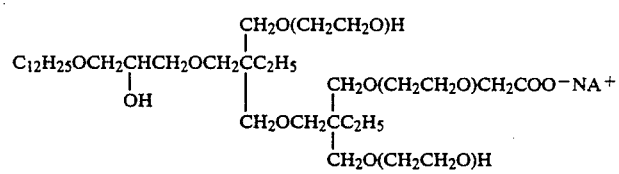
(d)

A = CH₂CH₂O, p = 2, m = 1 for each branch p, $R^{II}$ = CH₂, n = 1, B = COO⁻, q = 1, m = 1

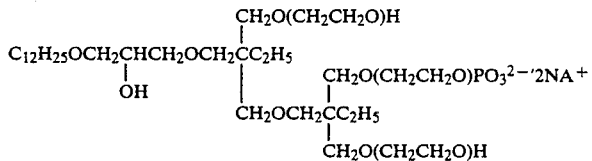
(e)

A = CH₂CH₂O, p = 2, m = 1 for each branch p, N = 0, B = PO₃²⁻, q = 1, m = 1

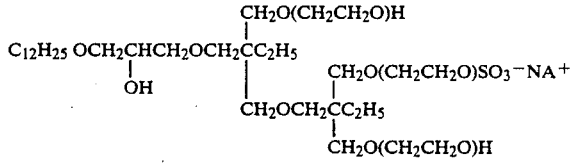
(f)

A = CH₂CH₂O, p = 2, m = 1 for each branch p, n = 0, B = SO₃⁻, q = 1, m = 1

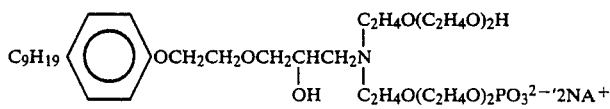
(g)

A = C₂H₄O, m = 2, p = 1, n = 0, B = PO₃²⁻, m = 2, q = 1

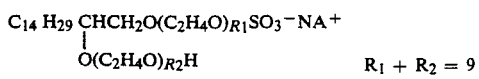
(h)

R₁ + R₂ = 9

A = C₂H₄O, m = R₂ for branch p, p = 1, B = SO₃⁻, n = 0, q = 1, m = R₁ for branch q, -continued

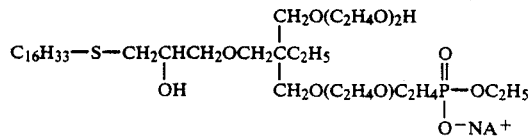 (i)

$A = (C_2H_4O)$, $m = 2$, $p = 1$, $B = -\overset{O}{\underset{O^-}{\overset{\|}{P}}}-OC_2H_5$, $n = 1$, $q = 1$, $m = 1$, $R^{II} = C_2H_4$

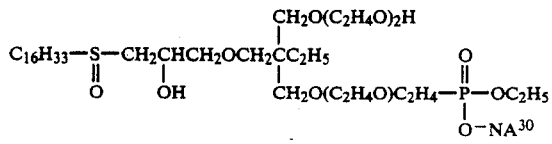 (j)

$A = C_2H_4O$, $p = 1$, $m = 2$, $B = -\overset{O}{\underset{O^-}{\overset{\|}{P}}}-OC_2H_5$, $n = 1$, $R^{II} = C_2H_4$, $q = 1$, $m = 1$

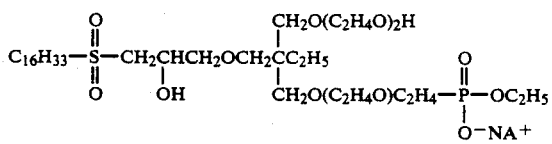 (k)

$A = C_2H_4O$, $m = 2$, $p = 1$, $B = -\overset{O}{\underset{O^-}{\overset{\|}{P}}}-OC_2H_5$, $n = 1$, $R^{II} = C_2H_4$, $q = 1$, $m = 1$

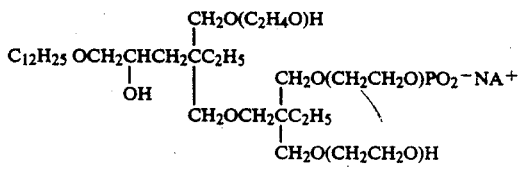 (l)

$A = C_2H_4O$, $p = 2$, $m = 1$ for each branch p and for the branch q, $n = 0$, $B = PO_2^-$, $q = 1$

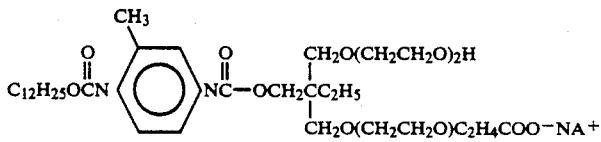 (m)

$A = CH_2CH_2O$, $m = 2$, $p = 1$, $B = COO^-$, $n = 1$, $R^{II} = C_2H_4$, $q = 1$, $m = 1$

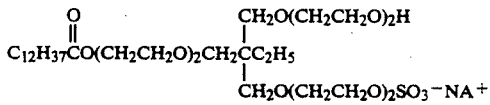 (n)

$A = CH_2CH_2O$, $m = 2$, $p = 1$, $q = 1$, $n = 0$, $B = SO_3^-$, $m = 2$

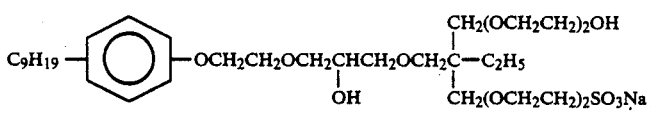 (o)

The surfactants of the present invention may be prepared by well-known reactions. A typical route of preparation is as follows: A hydroxyl containing compound, such as a fatty alcohol, is reacted with epichlorohydrin and the addition product formed is treated with alkali to reform a terminal oxirane ring. The product obtained is reacted with equimolar amounts of polyol, e.g., a tetraol. After completed reaction the product formed, in this case a triol, is ethoxylated to form a nonionic surfactant with branched hydrophilic part. A certain proportion of the terminal hydroxyl groups are then transformed into anionic groups by conventional methods.

Another method is first to react a polyol with an alkylene oxide to form an alkylene oxide adduct. This adduct is then reacted with, e.g., a hydrophobic monoisocyanate or a monocarboxylic acid, and the obtained nonionic compound is transformed with conventional method into the desired anionic compound.

The following example further illustrates the invention and represents a preferred embodiment thereof.

EXAMPLE

Phase volume studies were performed with oil, water and a series of surfactants and surfactant systems. North sea oil having an equivalent carbon number of C9 was used as the oil phase and synthetic North sea water was employed as the aqueous phase. The following surfactants and surfactant systems were tested:

(1) $C_9H_{19}$—⟨C$_6$H$_4$⟩—$(OCH_2CH_2)_3$—$SO_3^-Na^+$ (2) $C_{16}H_{33}$—$(OCH_2CH_2)_4$—$\overset{O}{\underset{OC_2H_5}{\overset{\|}{P}}}$—$O^-Na^+$ 3 $C_{12}H_{25}$—$(OCH_2CH_2)_2$—$OCH_2COO^-Na^+$.
4 Compound (a).
5 Compound (c).
6 Compound (d).
7 Compound (m).
8 Compound (n).
9 Compound (e).
10 Surfactant 1+sec butanol, 1:1 by weight.
11 Surfactant 2+sec butanol, 1:1 by weight.
12 Surfactant 3+isoamyl alcohol, 1:1 by weight.

The above surfactants and surfactant systems were tested at 20°, 50° and 80° C. The compositions used consisted of 48% by weight oil, 48 weight % water and 4 weight % of compound or system 1–12. In the table below the phase behaviour obtained after mixing of the components and equilibration for 24 h is indicated by the number of phases visible in the test tubes.

TABLE

| Surfactant/ | Number of phases | | |
|---|---|---|---|
| system | 20° C. | 50° C. | 80° C. |
| 1 | 2 | 2 | 2 |
| 2 | 2 | 2 | 2 |
| 3 | 2 | 2 | 2 |
| 4 | 3 | 2 | 2 |
| 5 | 3 | 3 | 3 |
| 6 | 3 | 3 | 3 |
| 7 | 3 | 3 | 3 |
| 8 | 3 | 3 | 3 |
| 9 | 3 | 3 | 3 |
| 10 | 3 | 3 | 2 |
| 11 | 3 | 3 | 3 |
| 12 | 3 | 3 | 2 |

As is seen from the table, three phase systems are obtained with the surface active compounds 4–9 in accordance with the invention, as well as with the co-surfactant containing systems 10, 11 and 12. The conventional surfactants alone (1, 2 and 3) give only two phase systems.

The three phase systems consisted of a lower phase which was almost pure brine, a surfactant-rich middle phase in the form of a microemulsion and an upper phase which was almost pure oil.

We claim:

1. In a process for recovering oil from an oil well wherein a microemulsion containing water, an oil component and a surfactant system is supplied to said oil well to chemically flood the oil well and increase the amount of oil that can be recovered therefrom, the improvement wherein the surfactant system consists essentially of a surface active compound which contains one hydrophobic group containing 9–50 carbon atoms and 2–6 separate hydrophilic end groups, at least one of said 2–6 separate hydrophilic end groups being a nonionic group obtained by reacting a compound having a reactive hydrogen atom with an alkylene oxide having 2–4 carbon atoms and at least one being an anionic group.

2. A process according to claim 1, wherein said surface active compound has a general formula $$R^I \begin{matrix} [O-(A)_m-H]_p \\ [O-(A)_m-(R^{II})_n\cdot B]_q \end{matrix}$$

wherein $R^I$ is a hydrophobic group containing 9–50 carbon atoms and optionally functional groups, $R^{II}$ is an alkylene or hydroxyalkylene group with 1–4 carbon atoms, A is an alkyleneoxy group derived from an alkylene oxide having 2–4 carbon atoms, m, which may be different for each branch (p and/or q), has an average value of 1–10, n is 0 or 1, p and q are 1–5, the sum p+q is 2–6, and B is an anionic group.

3. A process according to claim 1, wherein the anionic group of said surface active compound is selected from the group consisting of a carboxylate, phosphonate, sulphonate, sulphate, phosphate and phosphite.

4. A process according to claim 2, wherein said functional groups of said surface active compound are selected from the group consisting of ether, ester and hydroxyl.

5. A process according to claim 2, wherein said alkyleneoxy groups of said surface active compound is at least 50% ethyleneoxy groups.

6. A process according to claim 1, wherein said hydrophobic group of said surface active compound contains 12–35 carbon atoms.

7. A process according to claim 2, wherein the anionic group of said surface active compound is selected from the group consisting of a carboxylate, phosphonate, sulphonate, sulphate, phosphate and phosphite.

8. A process according to claim 3, wherein q is 1.

* * * * *